United States Patent
De Cicco et al.

(10) Patent No.: US 11,350,954 B2
(45) Date of Patent: Jun. 7, 2022

(54) INTRAVASCULAR ULTRASOUND (IVUS) AND FLOW GUIDED EMBOLISM THERAPY DEVICES SYSTEMS AND METHODS

(71) Applicant: KONINKLIJKE PHILIPS N.V., Eindhoven (NL)

(72) Inventors: Dino De Cicco, Carlsbad, CA (US); David Goodman, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 375 days.

(21) Appl. No.: 16/048,266

(22) Filed: Jul. 28, 2018

(65) Prior Publication Data

US 2019/0029702 A1  Jan. 31, 2019

Related U.S. Application Data

(60) Provisional application No. 62/538,331, filed on Jul. 28, 2017.

(51) Int. Cl.
*A61B 17/22* (2006.01)
*A61B 8/06* (2006.01)
(Continued)

(52) U.S. Cl.
CPC ............ *A61B 17/2202* (2013.01); *A61B 8/06* (2013.01); *A61B 8/12* (2013.01); *A61B 17/3207* (2013.01); *A61B 2017/00075* (2013.01); *A61B 2017/00106* (2013.01); *A61B 2017/22079* (2013.01); *A61B 2090/063* (2016.02); *A61B 2090/064* (2016.02); *A61B 2090/3784* (2016.02)

(58) Field of Classification Search
CPC .. A61B 8/06; A61B 8/085; A61B 8/12; A61B 17/2202; A61B 17/3207; A61B 2017/00075; A61B 2017/00106; A61B 2017/22079; A61B 2090/063; A61B 2090/064; A61B 2090/3784
See application file for complete search history.

(56) References Cited

U.S. PATENT DOCUMENTS 7,846,101 B2    12/2010  Eberle et al.
10,058,284 B2 *  8/2018  Hoseit ................ A61B 18/1492
(Continued)

FOREIGN PATENT DOCUMENTS

WO   WO-2005094283 A2 * 10/2005  ............... A61F 2/01
WO   WO-2014107727 A1 *  7/2014  ........... A61B 17/221
(Continued)

*Primary Examiner* — Boniface Ngathi N

(57) ABSTRACT

Embolism treatment devices, systems, and methods are provided. In one embodiment, an embolism treatment system includes a flexible elongate member configured to be positioned within a blood vessel of a patient, the flexible elongate member comprising a distal portion and a proximal portion; an ultrasound imaging component positioned at the distal portion and configured to emit ultrasound energy towards a blood clot within the blood vessel and collect an image signal representative of the blood clot; a treatment component positioned at the distal portion and configured to treat the blood clot; and a flow sensing component positioned at the distal portion and configured to determine a blood flow measurement within the blood vessel associated with the blood clot.

16 Claims, 5 Drawing Sheets

(51) Int. Cl.
  *A61B 8/12*      (2006.01)
  *A61B 17/3207*   (2006.01)
  *A61B 90/00*     (2016.01)
  *A61B 17/00*     (2006.01)

(56) References Cited

U.S. PATENT DOCUMENTS

| | | | |
|---|---|---|---|
| 2003/0199768 A1* | 10/2003 | Cespedes | A61B 5/02007 |
| | | | 600/473 |
| 2007/0232933 A1* | 10/2007 | Gille | A61B 8/467 |
| | | | 600/481 |
| 2009/0195514 A1* | 8/2009 | Glynn | A61B 8/469 |
| | | | 345/173 |
| 2010/0057097 A1* | 3/2010 | Ma | A61N 7/00 |
| | | | 606/128 |
| 2014/0180034 A1* | 6/2014 | Hoseit | A61B 5/0066 |
| | | | 600/301 |
| 2014/0236118 A1* | 8/2014 | Unser | A61M 5/1723 |
| | | | 604/503 |
| 2014/0276684 A1* | 9/2014 | Huennekens | A61B 17/320758 |
| | | | 606/7 |
| 2015/0313479 A1* | 11/2015 | Stigall | A61B 8/12 |
| | | | 600/467 |
| 2016/0302762 A1* | 10/2016 | Stigall | A61B 5/0066 |
| 2019/0029702 A1* | 1/2019 | De Cicco | A61B 8/085 |

FOREIGN PATENT DOCUMENTS

| | | | | |
|---|---|---|---|---|
| WO | WO-2015074018 A1 | * | 5/2015 | A61B 6/487 |
| WO | WO-2015074032 A1 | * | 5/2015 | A61M 37/0092 |
| WO | WO-2015076864 A1 | * | 5/2015 | A61N 1/327 |
| WO | WO-2016046710 A1 | * | 3/2016 | A61B 17/12172 |

* cited by examiner

INTRAVASCULAR ULTRASOUND (IVUS) AND FLOW GUIDED EMBOLISM THERAPY DEVICES SYSTEMS AND METHODS

TECHNICAL FIELD

The present disclosure relates generally to intraluminal devices, in particular, to providing intravascular ultrasound (IVUS) and flow guided treatment of venous thromboembolism (VTE) associated with pulmonary embolic events. For example, a catheter assembly can include a treatment component for treating a blood clot, an ultrasound imaging component for obtaining images of the blood clot before, during, and/or after the treatment, and a flow sensing component for measuring a blood flow measurement associated with the blood clot before, during, and/or after the treatment.

BACKGROUND

Pulmonary thromboemboli is a pulmonary embolism (PE) that may originate from a thrombus forms in central or deep veins, which has dislodged and occluded one or several pulmonary arteries. Some interventional techniques for treating PE may employ a catheter and guidewire type device to fragment and/or remove the PE from the occluded pulmonary artery so that a normal blood flow (e.g., a free flow or an effective flow) may be restored. In some instances, fluroscopy, which converts X-rays into video images, may be used to watch and guide the progress of a PE treatment procedure. However, fluroscopy may provide limited imaging capability and may be time-consuming. PE may be life-threatening and the time to restore blood flow may be critical. Thus, fluroscopy guided treatment may be not be optimal. In addition, fluroscopy may not be able to provide sufficient information for evaluating the completeness or effectiveness of a blockage removal.

SUMMARY

While existing fluroscopy guided treatment procedures have proved useful for treating PE, there remains a clinical need for improved systems and techniques for providing efficient PE treatment procedures and quantifying PE treatment results. Embodiments of the present disclosure provide an IVUS and flow guided embolic treatment of venous thromboembolism (VTE). For example, an IVUS and flow guided embolectomy device may include a flexible elongated member with an ultrasound imaging component, a flow sensing component, and a treatment component positioned at a distal portion of the device. In operation, the device is positioned into a vasculature of a patient. The ultrasound imaging component can capture images of a blood vessel and blood clots. The images may provide information associated with the position and characteristics of the blood clots. The treatment component can treat (e.g., remove or fragment) the blood clots. The flow sensing component can measure the blood flow (e.g., velocity) in the vessel. The blood flow measurements can quantify the result of the treatment.

In one embodiment, an embolism treatment system is provided. The embolism system includes a flexible elongate member configured to be positioned within a blood vessel of a patient, the flexible elongate member comprising a distal portion and a proximal portion; an ultrasound imaging component positioned at the distal portion and configured to emit ultrasound energy towards a blood clot within the blood vessel and collect an image signal representative of the blood clot; a treatment component positioned at the distal portion and configured to treat the blood clot; and a flow sensing component positioned at the distal portion and configured to determine a blood flow measurement within the blood vessel associated with the blood clot.

In some embodiments, the embolism system further comprises an interface coupled to the ultrasound imaging component and a display component, the interface configured to transmit the image signal to the display component for displaying an image of the blood clot. In some embodiments, the embolism system further comprises an interface coupled to the ultrasound imaging component and a processing component, the interface configured to transmit the image signal to the processing component for co-registering the image signal with a radiographic imaging signal representative of the blood vessel associated with the blood clot. In some embodiments, the embolism system further comprises an interface coupled to the flow sensing measurement and a display component, the interface configured to transmit the blood flow measurement to the display component for displaying the blood flow measurement. In some embodiments, the treatment component includes a therapeutic ultrasound component configured to emit ultrasound energy to fragment the blood clot. In some embodiments, the treatment component includes an aspiration component configured to remove the blood clot. In some embodiments, the treatment component includes a mechanical cutting component configured to fragment the blood clot. In some embodiments, the ultrasound imaging component includes an array of ultrasound transducers. In some embodiments, the embolism system further comprises an embolic protection component positioned at the distal portion of the flexible elongate member, the embolic protection component configured to restrict flow of blood clot fragments resulting from the treatment through the blood vessel. In some embodiments, the ultrasound imaging component and the flow sensing component include a common ultrasound transducer.

In one embodiment, a method of embolism treatment is provided. The method includes obtaining, via an ultrasound imaging component disposed at a distal portion of a flexible elongate member positioned within a vessel, an image representative of a blood clot within the vessel; treating, via a treatment component disposed at the distal portion of the flexible elongate member, the blood clot based on the image; and determining, via a flow sensing component disposed at the distal portion of the flexible elongate member, a blood flow measurement within the vessel.

In some embodiments, the method further includes characterizing the blood clot based on the image; and treating the blood clot based on the characterizing. In some embodiments, the characterizing includes determining an age of the blood clot based on at least one of a degree of structural organizational of the blood clot from the image or an intensity level of the blood clot from the image. In some embodiments, the determining includes determining the blood flow measurement before the treating. In some embodiments, the determining includes determining the blood flow measurement after the treating. In some embodiments, the method further comprises repeating the treating based on the blood flow measurement. In some embodiments, the method further comprises assessing an effectiveness of the treating by obtaining, via the ultrasound imaging component, another image of the vessel after the treating; and determining, via the flow sensing component, another blood flow measurement of the vessel after the treating. In some embodiments, the method further comprises co-registering the image obtained from the ultrasound imaging component with a radiographic image of the blood clot; and determining a position of the blood clot based on the co-registering. In some embodiments, the treating includes fragmenting the blood clot. In some embodiments, the treating includes removing the blood clot.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
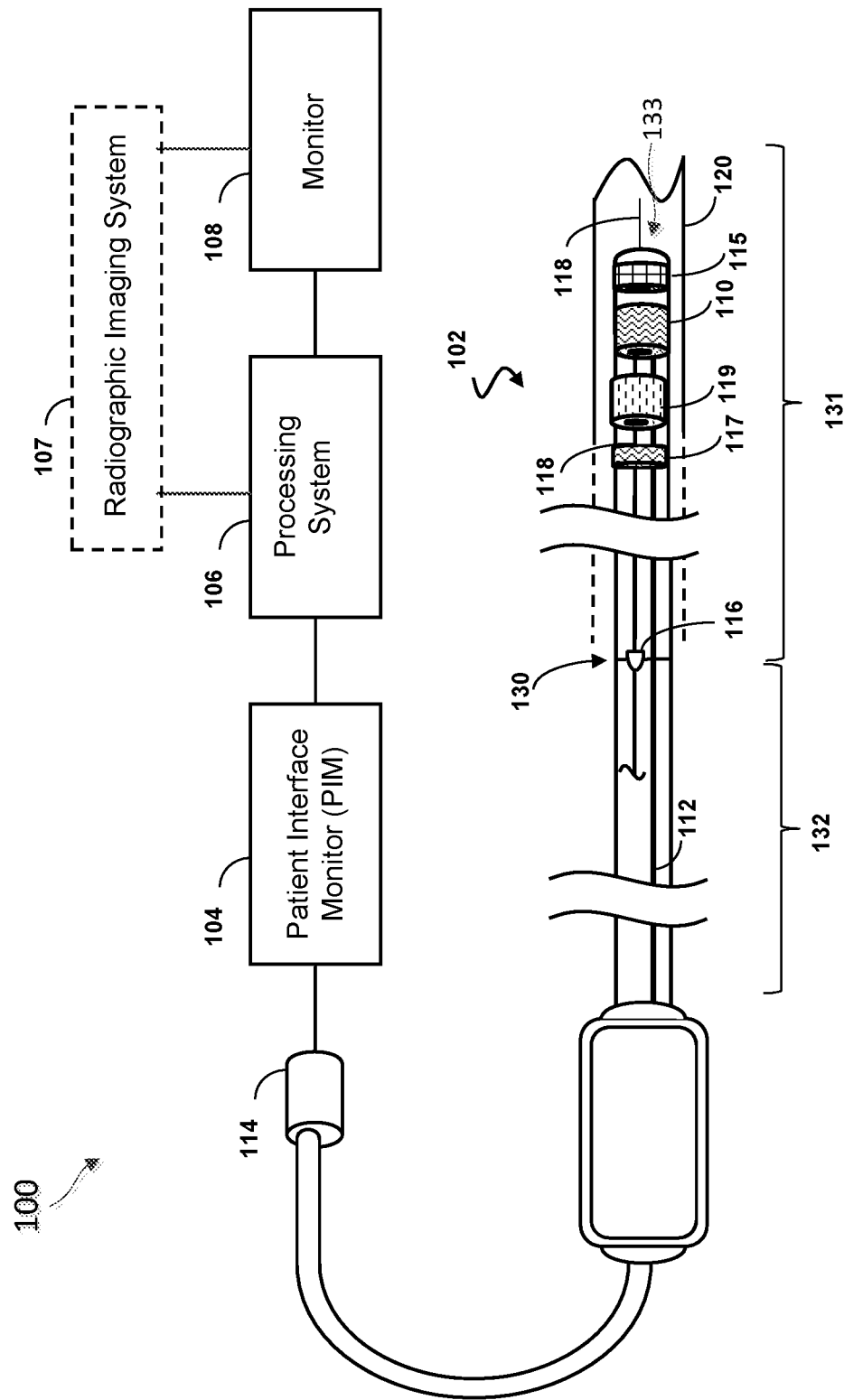
FIG. 1 is a schematic diagram of an embolism treatment system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an embolism treatment system 100, according to aspects of the present disclosure. The system 100 may include an intraluminal device 102 such as a catheter, guide wire, or guide catheter, a patient interface module (PIM) 104, a processing system 106, such as a console and/or a computer, and a monitor 108.

The intraluminal device 102 is an intravascular ultrasound (IVUS) and flow guided embolectomy device. The intraluminal device 102 may include a flexible elongate member sized and shaped for insertion into the vasculature of a patient. The flexible elongate member may include a distal portion 131 and a proximal portion 132. The intraluminal device 102 may include an imaging component 110, a treatment component 119, and a flow sensing component 117 mounted at the distal portion 131 near a distal end 133 of the intraluminal device 102. At a high level, the intraluminal device 102 may be inserted into a body lumen 120 of the patient. For example, the intraluminal device 102 can be inserted into a patient's vessel 120 to treat a blood clot formed in the vessel 120. For example, the imaging component 110 may capture images of the blood clot, the treatment component 119 may break down and/or remove the blood clot, and the flow sensing component 117 may measure a blood flow within the vessel 120 to provide a quantitative assessment of the presence of the blood clot and/or the efficacy of a treatment. The vessel 120 may be any artery or vein within a vascular system of a patient. In some embodiments, the vessel 120 may be a venous vessel within the lungs or legs of a patient. For example, the vessel 120 may be a pulmonary vessel.

In an embodiment, the imaging component 110 may include ultrasound transducers configured to emit ultrasonic energy towards the vessel 120. The ultrasonic energy is reflected by tissue structures and/or blood clots in the vessel 120 surrounding the imaging component 110. The reflected ultrasound echo signals are received by the ultrasound transducers in the imaging component 110. In some embodiments, the ultrasound transducers in the imaging component are phased-array transducers, which may be configured to emit ultrasound energy at a frequency of about 10 megahertz (MHz) to about 20 MHz. In some other embodiments, the imaging component 110 may be alternatively configured to include a rotational transducer to provide similar functionalities. The PIM 104 transfers the received echo signals to the processing system 106 where the ultrasound image is reconstructed and displayed on the monitor 108. For example, the strengths or the amplitudes of the echo responses may be converted to brightness or intensity levels for gray-scale image display. The ultrasound image can be used for determining the position of a blood clot and/or characterizing a blood clot (e.g., an age or acuteness of the blood clot). The processing system 106 can include a processor and a memory. The processing system 106 can be operable to facilitate the features of the system 100 described herein. For example, the processor can execute computer readable instructions stored on the non-transitory tangible computer readable medium.

The treatment component 119 is configured to remove blood clots in the vessel 120. For example, the treatment component 119 may include an ultrasound therapeutic component, an aspiration component, and/or a mechanical cutting component. An ultrasound therapeutic component can be configured to emit ultrasound energy at a certain frequency towards a blood clot, where the ultrasound energy may break down the blood clot. An aspiration component can be configured to remove or suck a blood clot or blood clot fragments from the blood flow passageway within the vessel 120. A mechanical cutting component can be configured to fragment a blood clot. In some embodiments, the mechanical cutting component may be a rotational cutting device.

The flow sensing component 117 is configured to sense and obtain flow measurements in the vessel 120. The flow sensing component 117 may include one or more flow sensors, pressure sensors, and/or transducers for measuring a blood flow (e.g., velocity) within the vessel 120. In an embodiment, flow sensing component 117 may include ultrasound transducers configured to emit ultrasound waves at an angle with respect to the vessel 120. The ultrasound waves may be backscattered by the moving blood flow travelling at a particular velocity and a particular direction in the vessel 120. The backscattered ultrasound waves are received by the ultrasound transducers in the flow sensing component 117. The frequencies of the received backscattered ultrasound waves are Doppler-shifted by an amount proportional to the blood flow velocity.

In an embodiment, the PIM 104 transfers the backscattered ultrasound data from the flow sensing component 117 to the processing system 106. The processing system 106 can analyze the data to determine the presence or absence, the direction, and the amount of fluid flow (e.g., blood flow) in the vessel 120. Doppler ultrasound measures the movement of objects through the emitted beam as a phase change in the received signal. When ultrasound waves are reflected from a moving structure (e.g., a red blood cell within a vessel 200), the wavelength and the frequency of the returning waves are shifted. If the moving structure is moving toward the transducer, the frequency increases. If the moving structure is moving away from the transducer, the frequency decreases.

In some embodiments, the processing system 106 can employ the Doppler Equation:

$$\Delta f = (2f0 V \cos \theta)/C \qquad (1)$$

where $\Delta f$ is the frequency shift, f0 is the frequency of the transmitted wave, V is the velocity of the reflecting object (e.g., a red blood cell), $\theta$ is the angle between the incident wave and the direction of the movement of the reflecting object (i.e., the angle of incidence), and C is the velocity of sound in the medium. The frequency shift is maximal when the transducer is oriented parallel to the direction of the blood flow and the $\theta$ is zero degrees (cos 0=1). The frequency shift is absent when the transducer is oriented perpendicular to the direction of the blood flow and the 0 is 90 degrees (cos 90=0). Higher Doppler frequency shifts are obtained when the velocity is increased, the incident wave is more aligned to the direction of blood flow, and/or when a higher frequency is emitted.

Thus, the blood flow velocity may be determined based on Equation (1). The blood flow velocity measurements may be indicative of a blockage in the vessel 120 due to a blood clot and/or whether an adequate blood flow has been restored after a treatment.

The imaging component 110 and the flow component 117 can be used in conjunction with the treatment component 119 to guide a treatment procedure, for example, before, during, and/or after the treatment procedure. While FIG. 1 illustrates the imaging component 110 positioned distal to the treatment component 119 and the flow sensing component 117 positioned proximal to the treatment component 119, the imaging component 110, the treatment component 119, and the flow sensing component 117 may be arranged in any suitable order at the distal portion 131 of the intraluminal device 102. For example, the imaging component 110 may be positioned proximal to the treatment component 119 and the flow sensing component 117 may be positioned distal to the treatment component 119.

While the imaging component 110 and the flow sensing component 117 are shown as separate components, in some embodiments, the imaging component 110 and the flow sensing component 117 may be an integrated device. In an embodiment, the integrated device can include common ultrasound transducers configured for both imaging (e.g., based on brightness-mode processing) and flow measurements (e.g., based on Doppler processing).

The PIM 104 facilitates communication of signals between the processing system 106 and the imaging component 110, the treatment component 119, and/or the flow sensing component 117 included in the intraluminal device 102. In some embodiments, the PIM 104 performs preliminary processing of the echo data prior to relaying the echo data to the processing system 106. In examples of such embodiments, the PIM 104 performs amplification, filtering, and/or aggregating of the echo data. In an embodiment, the PIM 104 also supplies high- and low-voltage direct current (DC) power to support operation of the device 102 including circuitry within the imaging component 110, the treatment component 119, and/or the flow sensing component 117.

In an embodiment, the processing system 106 receives the echo data from the imaging component 110 and/or transmits controls to the imaging component 110 by way of the PIM 104. The processing system 106 processes the echo data to reconstruct an image of the tissue structures in the vessel 120 surrounding imaging component 110. The processing system 106 outputs image data such that an image of the vessel 120, such as a cross-sectional image of the vessel 120, is displayed on the monitor 108.

In an embodiment, the processing system 106 receives blood flow measurement data from the flow sensing component 117 and/or transmits controls to the flow sensing component 117 by way of the PIM 104. The processing system 106 processes the blood flow measurement data to provide a quantitative value associated with the blood flow, such as a velocity of the blood flow, and output the quantitative value for display on the monitor 108.

In some embodiments, the intraluminal device 102 may further include an embolic protection component 115 positioned near the distal end 133. The embolic protection component 115 is configured to capture or remove debris or blood clot fragments that become dislodged during a treatment procedure. Embolic debris may flow downstream and block other vessels resulting in procedural complications or poor treatment outcomes. In some embodiments, the embolic protection component 115 may include an expandable mesh, filter, or basket.

In some embodiments, the system 100 may further include a radiographic imaging system 107, such as a fluroscopic system, in communication with the processing system 106 and the monitor 108. The radiographic imaging system 107 can be configured to obtain a radiographic imaging view of the vessel 120 for display on the monitor 108. The radiographic imaging view may provide information associated with the movements of the vessel 120, blood flow within the vessel 120, and/or a blood clot within the vessel 120. In such embodiments, the radiographic imaging system 107 can be used in conjunction with the imaging component 110 to determine a position of a blood clot and/or a characteristic of the blood clot. For example, radiographic imaging signals captured from the radiographic imaging system 107 can be co-registered with image signals captured from the imaging component 110.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 includes the imaging component 110 near the distal end 133 of the intraluminal device 102 and an electrical cable 112 extending along the longitudinal body of the intraluminal device 102. The cable 112 is a transmission line bundle including a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used.

The cable 112 terminates in a PIM connector 114 at a proximal end of the intraluminal device 102. The PIM connector 114 electrically couples the cable 112 to the PIM 104 and physically couples the intraluminal device 102 to the PIM 104. In an embodiment, the intraluminal device 102 further includes a guide wire exit port 116 disposed near a junction 130 at which the distal portion 131 is coupled to the proximal portion 132. Accordingly, in some instances the intraluminal device 102 is a rapid-exchange catheter. The guide wire exit port 116 allows a guide wire 118 to be inserted towards the distal end 133 in order to direct the intraluminal device 102 through the vessel 120.

Figure 2:
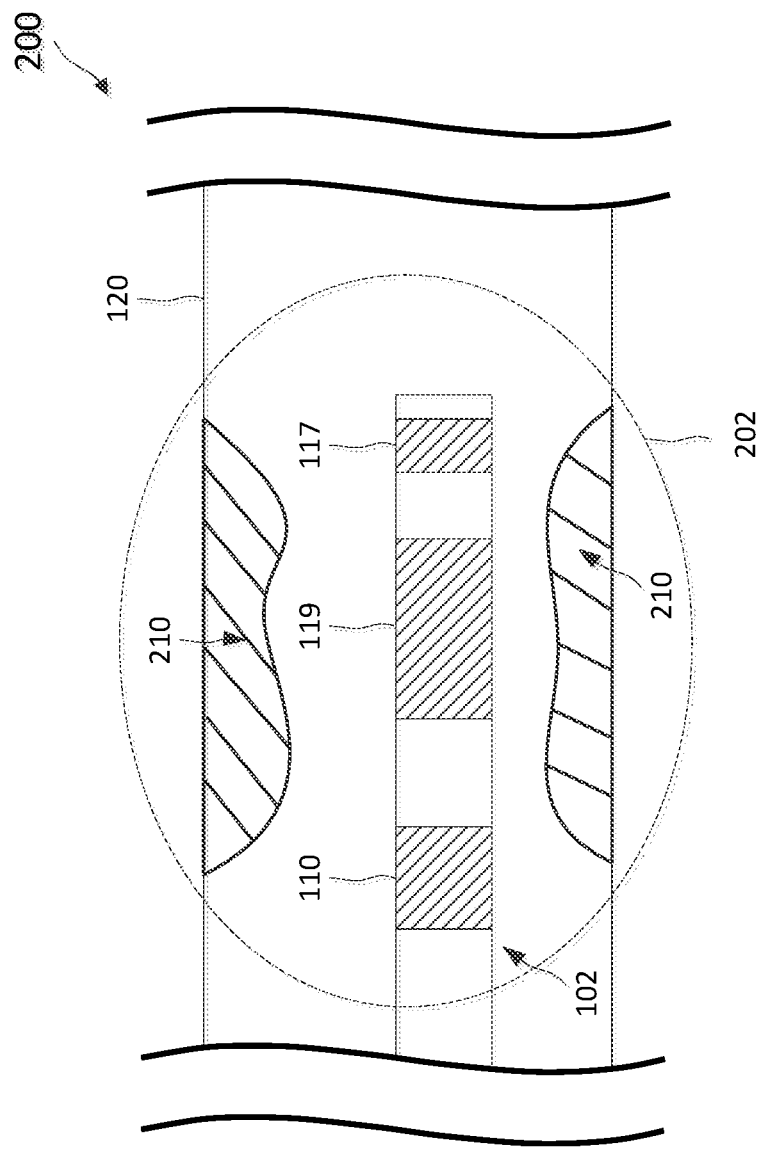
FIG. 2 is a schematic diagram illustrating an embolism treatment scenario, according to aspects of the present disclosure.

FIG. 2 is a schematic diagram illustrating an embolism treatment scenario 200, according to aspects of the present disclosure. The scenario 200 illustrates a side view of the intraluminal device 102 inserted within the vessel 120, wherein the distal portion of the intraluminal device 102 is at a position proximal to blood clots 210. The blood clots 210 are formed adjacent to the walls of the vessel 120. In some instances, the blood clots 210 may be attached to the walls of the vessel 120. The blood clots 210 may include an organized structure indicative of acute or aged blood clots. For example, the blood clots 210 may have been formed in the vessel 120 for a period longer than about two weeks to about one month.

During operation, the imaging component 110 may emit ultrasound energy towards the blood clots 210 and capture echo responses reflected by surrounding tissue structure of the vessel 120 and the blood clots 210. The echo responses can be processed to reconstruct images of the vessel 120 and the blood clots 210. The strength of the ultrasound echo reflected from a blood clot is proportional to the brightness of the reconstructed grey scale image. That is, the stronger the ultrasound echo is, the brighter the grey scale image will be. Thus, the blood clots 210 may appear as bright structures in the reconstructed image. A clinician or a physician may identify the presence the blood clots 210 based on the reconstructed image. The clinician or the physician may characterize the blood clots 210 based on the reconstructed image. For example, the clinician or the physician may determine an age or a degree of structural organization of the blood clots 210 based on the position and/or the brightness of the blood clots 210 and subsequently select a suitable treatment mode for the patient. For example, some blood clots may be more amenable to treatment by a pharmacological agent whereas other treatments may require a mechanical cutting embolectomy device.

The treatment component 119 may remove and/or fragment the blood clots. The clinician or physician may position the intraluminal device 102 based on the reconstructed image such that the treatment component 119 is positioned for delivering a treatment. The treatment component 119 may remove the blood clots 210 by emitting ultrasound energy towards the blood clots 210 to break down the blood clots 210, applying mechanical mechanisms to cut and remove the blood clots 210, and/or applying aspiration and extraction to remove the blood clots. In some embodiments, the treatment component 119 can deliver a pharmacological agent to treat the blood clot.

The flow sensing component 117 may measure blood flow velocity within the vessel 120. For example, the presence of the blood clots 210 may restrict blood flow through the passage area 202, and thus the blood flow velocity may be low. In some instances, when the size of the blood clots 210 is sufficiently large, a complete blockage can occur with no blood flow through the passage area 202. As the treatment component 119 treats the blood clots, the blood flow may be restored to a normal flow or an effective flow through the passage area 202. Thus, the blood flow velocity can provide a quantitative assessment of the treatment procedure. The flow sensing component 117 may repeatedly measure the blood flow velocity during the treatment and the clinician or the physician may repeatedly operate or activate the treatment component 119 based on the blood flow measurements until an adequate blood flow is restored in the vessel 120. After the completion of the treatment procedure, the flow sensing component 117 may be configured to obtain a post-treatment measurement and the imaging component 110 may be configured to obtain a post-treatment image to confirm the effectiveness or completeness of the treatment procedure.

In some embodiments, the intraluminal device 102 may be repositioned or advanced to another occluded portion of the vessel 120 or another vessel in a venous artery branch and repeat the treatment procedure. The integration of the imaging component 110 and the flow sensing component 117 with the treatment component 119 on the same device 102 can guide the treatment and provide quantitative measure of the effectiveness of the treatment.

Figure 3:
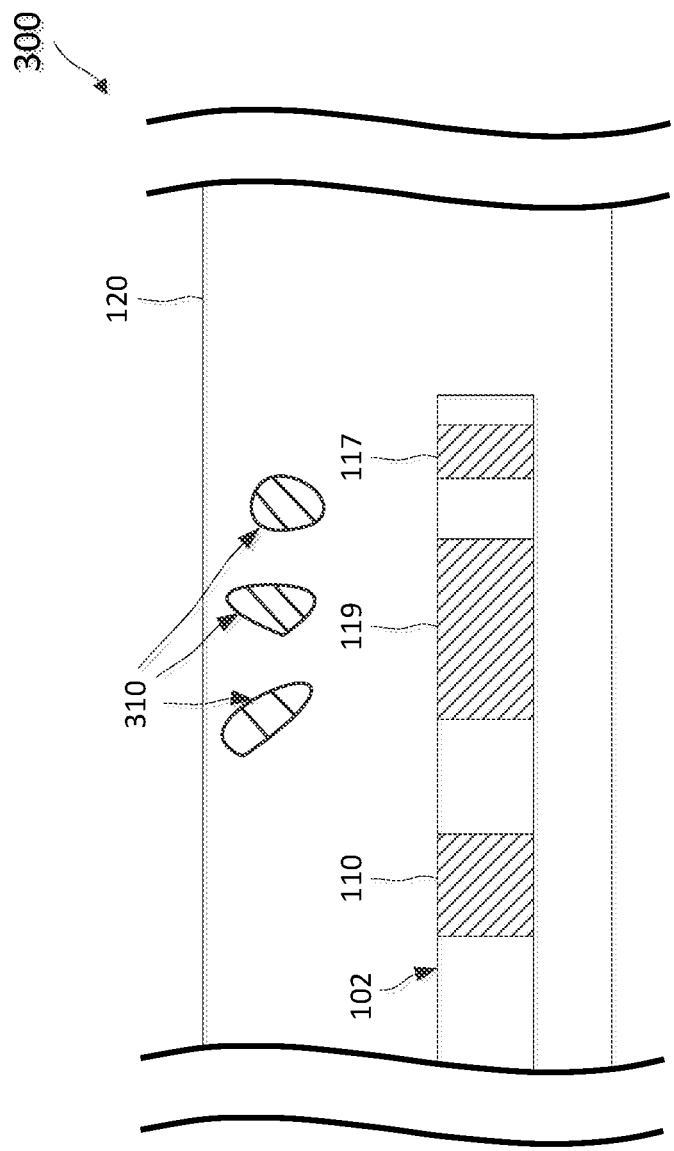
FIG. 3 is a schematic diagram illustrating an embolism treatment scenario, according to aspects of the present disclosure.

FIG. 3 is a schematic diagram illustrating an embolism treatment scenario 300, according to aspects of the present disclosure. The scenario 300 illustrates a side view of the intraluminal device 102 inserted within the vessel 120, where the distal portion of the intraluminal device 102 is at a position proximal to blood clots 310. The blood clots 310 are formed within the vessel 120. The blood clots 310 may include a scattered structure instead of an organized structure as in the scenario 200. The scattered structure may be indicative of freshly formed blood clots, for example, formed less than about one week.

The imaging component 110, the flow sensing component 117, and the treatment component 119 may operate together to remove the blood clots 310 using similar mechanisms as described in the scenario 200. The blood clots 310 may appear as scattered spots with low-intensity or less brightness in an image obtained from the imaging component 110.

Figure 4:
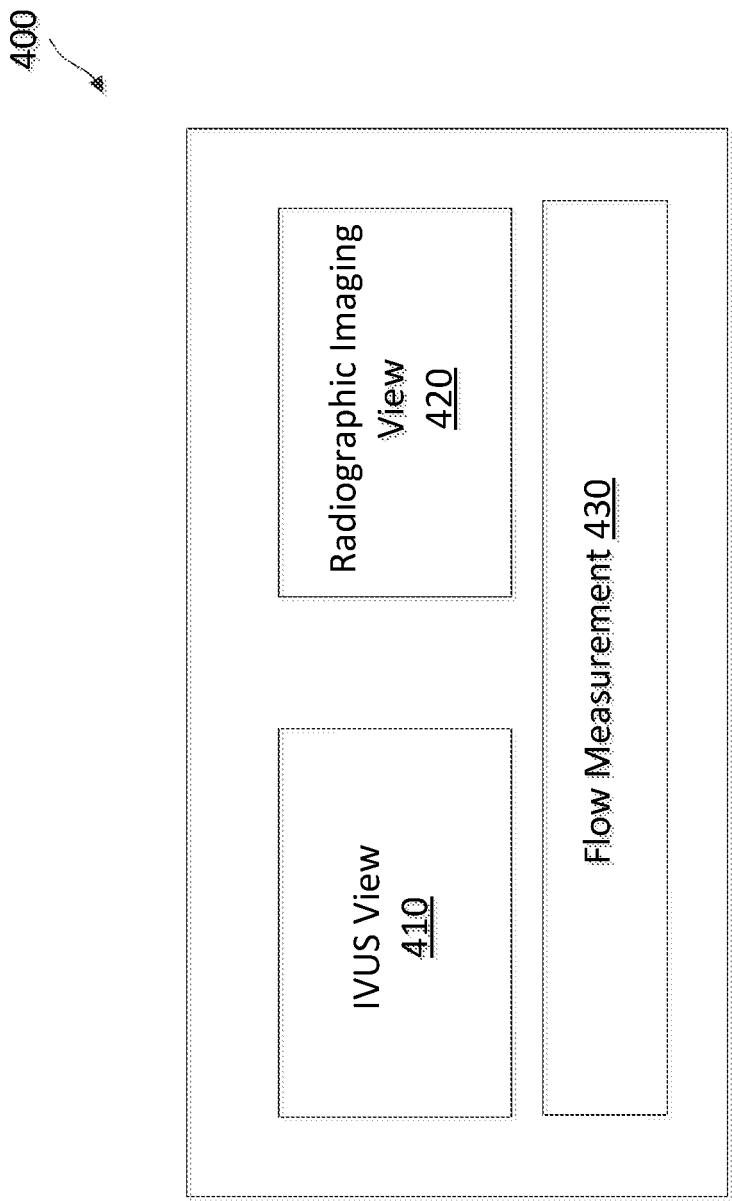
FIG. 4 is a schematic diagram of a graphical user interface for use in an embolism treatment system, according to aspects of the present disclosure.

FIG. 4 is a schematic diagram of a graphical user interface 400 for use in an embolism treatment system, such as the system 100, according to aspects of the present disclosure. For example, the graphical user interface 400 may be displayed on the monitor 108. The graphical user interface 400 includes an IVUS view 410, a radiographic imaging view 420, and a flow measurement view 430.

The IVUS view 410 may display an image of the vessel 120 reconstructed from image signals received from the imaging component 110. The image may include a cross-sectional view of the vessel 120, for example, including the blood clots 210 or 310. As described above, the aged blood clots 210 may appear as an organized, high-intensity structure in the image, while the freshly formed blood clots 310 may appear as scattered low-intensity spots.

The radiographic imaging view 420 may display a continuous stream of images (e.g., similar to a video) of the vessel 120 reconstructed from radiographic imaging signals received from the radiographic imaging system 107. The continuous stream of images may show movements of the vessel 120, movements of the blood flow in the vessel 120, and/or movements of the blood clots 210 or 310. In some embodiments, the IVUS view 410 and the radiographic imaging view 420 may be co-registered to display the same portion of the vessel 120 at the same time. Thus, both the IVUS view 410 and the radiographic imaging view 420 may guide a clinician or a physician during a treatment procedure.

The flow measurement view 430 may display a blood flow velocity within the vessel 120 computed or obtained from measurements received from the flow sensing component 117. In some embodiments, the flow measurement view 430 may display a blood flow velocity measurement at particular time. In some embodiments, the flow measurement view 430 may display a graph or plot of the blood flow velocities as a function of time (e.g., before, during, and/or after a treatment) or as a function of a length of the vessel 120 around the blockage area (e.g., distal to the passage area 202 and proximal to the passage area 202). In some embodiments, the flow measurement view 430 may include a real-time color map display of blood flow velocity and/or blood flow direction. In some embodiments, the flow measurement view 430 can include one or more numerical values, such as a numerical value of the blood flow velocity.

Figure 5:
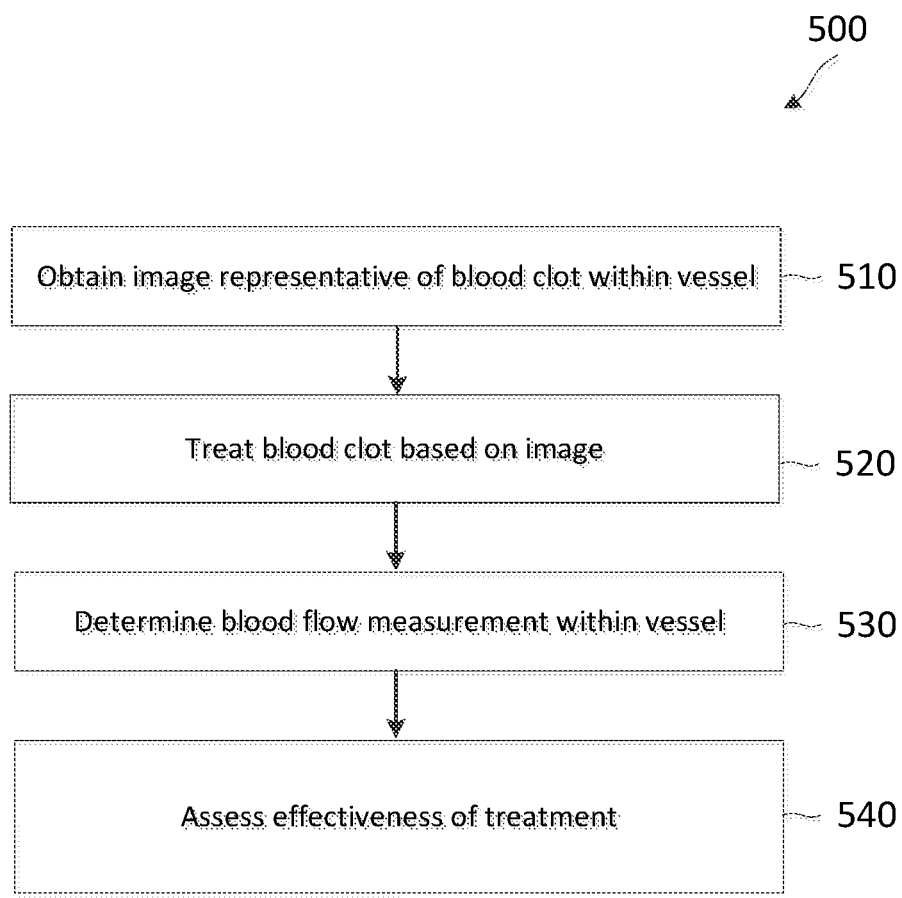
FIG. 5 is a flow diagram of a method of treating an embolism, according to aspects of the disclosure.

FIG. 5 is a flow diagram of a method 500 of treating an embolism, according to aspects of the disclosure. Steps of the method 500 can be executed by the system 100. The method 500 may employ similar mechanisms as in the scenarios 200 and 300 as described with respect to FIGS. 2 and 3, respectively. As illustrated, the method 500 includes a number of enumerated steps, but embodiments of the method 500 may include additional steps before, after, and in between the enumerated steps. In some embodiments, one or more of the enumerated steps may be omitted or performed in a different order.

At step 510, the method 500 includes obtaining an image representative of a blood clot (e.g., the blood clots 210 and 310) within a vessel (e.g., the vessel 120). For example, the intraluminal device 102 may be positioned within the vessel proximal to the blood clot and the imaging component 110 may be used to generate the image.

At step 520, the method 500 includes treating the blood clot based on the image. For example, the blood clot may be characterized based on the image and a treatment mode may be selected for treating the blood clot. As described above, the appearance of the brightness or intensity levels, the degree of structural organization, and/or the position of the blood clot in the image can be indicative of the age of the blood clot. Different treatment mode may be applied to treat blood clots of different age. For example, the treatment component 119 may be used to remove and/or fragment the blood clot.

At step 530, the method 500 includes determining a blood flow measurement within the vessel. For example, the flow sensing component 117 may be used to measure the blood flow velocity in the vessel. The steps 520 and 530 may be repeated, where the treatment may be performed iteratively and the flow sensing component 117 may be used to measure the blood flow velocity between each treatment iteration. For example, the step 530 may be performed before and/or after each treatment iteration and the treatment may be repeated until an adequate blood flow is restored in the vessel. In some embodiments, the intraluminal device 102 may be repositioned and the steps 510 to 530 may be repeated.

At step 540, the method 500 includes assessing the effectiveness of the treatment. For example, after the treatment is completed, the steps of 510 and 530 may be repeated. The blood flow velocity may provide a quantitative measure of the effectiveness of the treatment. For example, a slow flow velocity may be obtained before the treatment and an improved or increased flow velocity may be obtained after the treatment. In some embodiments, the method 500 may employ a radiographic imaging system 107 to obtain a radiographic image signal of the blood clot, co-register the radiographic image signal with the image obtained from the imaging component 110, and determine the position of the blood clot based on the co-registering.

In some instances, the system 106 can receive ultrasound imaging data from the ultrasound imaging element and flow related data from the flow sensing component. The system 106 can transmit controls signals to the ultrasound imaging element and/or the flow sensing component. The system 106 can generate display data based on the received ultrasound imaging data and the flow related data. The display data can be displayed by a monitor 108 in communication with the system 106. A doctor can determine how to the treat the vessel using the treatment element. In some instances, the system 106 can transmit control signals to the treatment element to control how the treatment is applied.

Aspects of the present disclosure can provide several benefits. For example, the integration of the ultrasound imaging component 110 and the flow sensing component 117 with the treatment component 119 in an embolectomy device can guide a clinician or physician in determining, performing, and assessing a treatment. Incorporating the ultrasound imaging component 110, the flow sensing component 117, and the treatment component 119 in a single device advantageously reduces the number of different catheters that need to be inserted and/or removed from the patient during a procedure. This can increase efficiency during the procedure, which is a benefit for patient health. The use of the ultrasound imaging component 110 can provide sufficient imaging quality for assessing or characterizing the blood clots. The use of the flow sensing component 117 can provide quantitative measures of the blood flow restored from the treatment. The integration can provide a more efficient workflow, where a clinician or physician may determine, treat, and assess with a single device insertion instead of exchanging different devices (e.g., an imaging catheter, a flow guide wire, and a treatment catheter). Thus, the disclosed embodiment can improve the efficiency of PE treatment procedures. The quantitative measures can improve the confidence levels of PE treatment procedures. While the disclosed embodiments are described in the context of treating blood clots or thrombus in pulmonary arteries, the disclosed embodiments can be applied to other arteries.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pulmonary embolism treatment system, comprising:
   a flexible elongate member configured to be positioned within a pulmonary blood vessel of a lung of a patient, the flexible elongate member comprising a distal portion and a proximal portion;
   an embolic protection component positioned at the distal portion of the flexible elongate member, the embolic protection component configured to restrict flow of blood clot fragments through the pulmonary blood vessel;

an ultrasound imaging component positioned at the distal portion and configured to emit ultrasound energy towards a blood clot within the pulmonary blood vessel of the lung of the patient and collect an image signal representative of the blood clot;

an embolic treatment component positioned at the distal portion proximal to the ultrasound imaging component and configured to treat the blood clot;

a flow sensing component positioned at the distal portion, the flow sensing component including one or more flow sensors configured to determine blood flow measurement as a function of time within the pulmonary blood vessel of the lung of the patient;

a display; and a processing component configured to present, on the display, simultaneous real-time presentations of the image of the blood clot within the pulmonary blood vessel generated from the image signal representative of the blood clot obtained by the ultrasound imaging component, a radiographic imaging view displaying a continuous stream of radiographic images of the pulmonary blood vessel, and a graph or plot of the blood flow measurement as a function of time.

2. The system of claim 1, further comprising an interface coupled to the ultrasound imaging component and the processing component, the interface configured to transmit the image signal to the processing component for co-registering the image signal with a radiographic imaging signal from which the radiographic images of the pulmonary blood vessel are generated.

3. The system of claim 1, wherein the treatment component includes a therapeutic ultrasound component configured to emit ultrasound energy to fragment the blood clot.

4. The system of claim 1, wherein the treatment component includes an aspiration component configured to remove the blood clot.

5. The system of claim 1, wherein the treatment component includes a mechanical cutting component configured to fragment the blood clot.

6. The system of claim 1, wherein the ultrasound imaging component includes an array of ultrasound transducers.

7. The system of claim 1, wherein the embolic protection component comprises an expandable mesh.

8. A method of treatment of a pulmonary embolism, the method comprising:

obtaining, via an ultrasound imaging component disposed at a distal portion of a flexible elongate member positioned within a pulmonary vessel in a lung, an image of a blood clot within the pulmonary vessel;

treating, via a treatment component disposed at the distal portion of the flexible elongate member, the blood clot based on the image;

restricting, with an embolic protection component positioned at the distal portion of the flexible elongate member, flow of blood clot fragments resulting from the treatment through the blood vessel;

determining, via a flow sensing component disposed at the distal portion of the flexible elongate member, a blood flow measurement within the pulmonary vessel as a function of time; and providing on a display simultaneous real-time presentations of the image of the blood clot within the pulmonary vessel obtained by the ultrasound imaging component, a radiographic imaging view displaying a continuous stream of radiographic images of the pulmonary vessel, and a graph or plot of the blood flow measurement within the pulmonary vessel as a function of time.

9. The method of claim 8, further comprising:

characterizing the blood clot based on the image of the blood clot within the pulmonary vessel obtained by the ultrasound imaging component; and treating the blood clot based on the characterizing.

10. The method of claim 9, wherein the characterizing includes determining an age of the blood clot based on at least one of a degree of structural organizational of the blood clot from the image of the blood clot within the pulmonary vessel obtained by the ultrasound imaging component or an intensity level of the blood clot from the image of the blood clot within the pulmonary vessel obtained by the ultrasound imaging component.

11. The method of claim 8, wherein the determining includes determining the blood flow measurement before the treating.

12. The method of claim 8, wherein the determining includes determining the blood flow measurement after the treating.

13. The method of claim 8, further comprising repeating the treating based on the blood flow measurement within the pulmonary vessel as a function of time.

14. The method of claim 8, further comprising:

co-registering the image of the blood clot within the pulmonary vessel obtained by the ultrasound imaging component with the continuous stream of radiographic images of the pulmonary vessel; and determining a position of the blood clot based on the co-registering.

15. The method of claim 8, wherein the treating includes fragmenting the blood clot.

16. The method of claim 8, wherein the treating includes removing the blood clot.

* * * * *